US008765910B2

(12) United States Patent
Rissom et al.

(10) Patent No.: US 8,765,910 B2
(45) Date of Patent: Jul. 1, 2014

(54) METHOD FOR AMIDATING POLYPEPTIDES WITH BASIC AMINO ACID C-TERMINALS BY MEANS OF SPECIFIC ENDOPROTEASES

(75) Inventors: Sebastian Rissom, Hofheim (DE); Paul Habermann, Frankfurt am Main (DE); Christophe Salagnad, Chatellerault (FR); Frank Zocher, Alsbach-Hahnlein (DE); Laure Landric-Burtin, Athis Mons (FR)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1680 days.

(21) Appl. No.: 12/065,643

(22) PCT Filed: Sep. 13, 2006

(86) PCT No.: PCT/EP2006/008903
§ 371 (c)(1),
(2), (4) Date: Apr. 21, 2010

(87) PCT Pub. No.: WO2007/036299
PCT Pub. Date: Apr. 5, 2007

(65) Prior Publication Data
US 2010/0311112 A1     Dec. 9, 2010

(30) Foreign Application Priority Data
Sep. 27, 2005  (DE) .................. 10 2005 046 113

(51) Int. Cl.
| C07K 1/36 | (2006.01) |
| C07K 1/107 | (2006.01) |
| C07K 14/00 | (2006.01) |
| A61K 38/16 | (2006.01) |
| C07K 1/00 | (2006.01) |

(52) U.S. Cl.
CPC .. *C07K 1/00* (2013.01); *A61K 38/16* (2013.01)
USPC ....... 530/333; 530/324; 435/69.1; 435/252.3; 514/6.9; 514/21.3

(58) Field of Classification Search
None
See application file for complete search history.

(56) References Cited

U.S. PATENT DOCUMENTS

| 5,332,664 | A | * | 7/1994 | Craig et al. ................... 435/69.4 |
| 5,416,073 | A | * | 5/1995 | Coy et al. ....................... 514/4.8 |
| 5,496,924 | A | * | 3/1996 | Habermann et al. ........... 530/350 |
| 5,635,371 | A | * | 6/1997 | Stout et al. ..................... 435/69.1 |
| 7,455,987 | B1 | * | 11/2008 | Habermann et al. ........... 435/69.1 |
| 7,939,293 | B2 | * | 5/2011 | Habermann et al. ........... 435/68.1 |
| 8,048,854 | B2 | * | 11/2011 | Habermann et al. ............ 514/6.3 |
| 2003/0028001 | A1 | * | 2/2003 | Habermann ..................... 536/23.1 |
| 2009/0192073 | A1 | * | 7/2009 | Habermann et al. ............... 514/3 |
| 2011/0077197 | A1 | * | 3/2011 | Habermann et al. ............ 514/6.4 |
| 2011/0173722 | A1 | * | 7/2011 | Habermann et al. ........... 800/295 |

FOREIGN PATENT DOCUMENTS

| EP | 0490249 B1 | 6/1992 |
| WO | WO 2004/035623 A2 | 4/2004 |
| WO | WO 2006/015879 A1 | 2/2006 |
| WO | WO 2006/058620 A2 | 6/2006 |

OTHER PUBLICATIONS

Schellenberger, V., et al., 1991, "Protease-catalyzed kinetically controlled peptide synthesis", Angewandte Chemie, International Edition, vol. 30, No. 11, pp. 1437-1449.*
Bongers, J., et al., 1992, "Semisynthesis of human growth hormone-releasing factor by trypsin-catalyzed coupling of leucine amide to a C-terminal acid precursor", International Journal of Peptide and Protein Research, vol. 40, Nos. 3/4, pp. 268-273.*
Davey, M. W., et al., 1995, "Trypsin-mediated semisynthesis of salmon calcitonin", International Journal of Peptide and Protein Research, vol. 45, No. 4, pp. 380-385.*
Thorkildsen, Christian et al., "Glucagon-Like Peptide 1 Receptor Agonist ZP10A Increases Insulin mRNA Expression and Prevents Diabetic Progression in db/db Mice," The Journal of Pharmacology and Experimental Therapeutics (2003), vol. 307, No. 2, pp. 490-496.
Schellenberger, V. et al., "Attempts for Quantifying the S' Subsite Specificity of Serine Proteases," Advances in the Biosciences (1987), vol. 65, pp. 159-166.
International Preliminary Report on Patentability dated Apr. 15, 2008 issued in PCT/EP2006/008903.
International Search Report dated Mar. 29, 2007 received from the European Patent Office from related International Application No. PCT/EP2006/008903.

* cited by examiner

Primary Examiner — Manjunath Rao
Assistant Examiner — William W Moore
(74) Attorney, Agent, or Firm — Scully, Scott, Murphy & Presser, P.C.

(57) ABSTRACT

The invention relates to a method for producing C-terminal amidated dibasic or polybasic peptides, consisting in reacting two peptides in the presence of trypsin biologically active enzymes and, if necessary, in purifying the thus obtainable compounds of formula (I) by means of protein chemistry.

5 Claims, No Drawings

SEQUENCE LISTING

```
<160> NUMBER OF SEQ ID NOS: 21

<210> SEQ ID NO 1
<211> LENGTH: 44
<212> TYPE: PRT
<213> ORGANISM: artificial sequence
<220> FEATURE:
<223> OTHER INFORMATION: description of the artificial sequence:
      exendin-4 derivative

<400> SEQUENCE: 1

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Ser Lys Lys Lys Lys Lys
         35                  40

<210> SEQ ID NO 2
<211> LENGTH: 40
<212> TYPE: PRT
```

```
<213> ORGANISM: artificial sequence
<220> FEATURE:
<223> OTHER INFORMATION: description of the artificial sequence:
      exendin-4-derivat

<400> SEQUENCE: 2

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Ser Lys Lys
         35                  40

<210> SEQ ID NO 3
<211> LENGTH: 40
<212> TYPE: PRT
<213> ORGANISM: artificial sequence
<220> FEATURE:
<223> OTHER INFORMATION: description of the artificial sequence:
      exendin-4-derivat

<400> SEQUENCE: 3

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Ser Lys Arg
         35                  40

<210> SEQ ID NO 4
<211> LENGTH: 44
<212> TYPE: PRT
<213> ORGANISM: artificial sequence
<220> FEATURE:
<223> OTHER INFORMATION: description of the artificial sequence:
      exendin-4-derivat

<400> SEQUENCE: 4

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Arg
         35                  40

<210> SEQ ID NO 5
<211> LENGTH: 40
<212> TYPE: PRT
<213> ORGANISM: artificial sequence
<220> FEATURE:
<223> OTHER INFORMATION: description of the artificial sequence:
      exendin-4-derivat

<400> SEQUENCE: 5

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Ser Arg Lys
         35                  40

<210> SEQ ID NO 6
<211> LENGTH: 192
```

```
<212> TYPE: DNA
<213> ORGANISM: artificial sequence
<220> FEATURE:
<223> OTHER INFORMATION: description of the artificial sequence: gene
      for sequence ID No. 7

<400> SEQUENCE: 6 tttttaagc ttgcacggtg aaggtacctt cacctccgac ctgtccaaac agatggaaga      60
agaagctgtt cgtctgttca tcgaatggct gaaaaacggt ggtccgtcct ccggtgctcc    120
gccttcgaaa aagaagaaaa agtgataata gcatgcacgt gcggccgcac ctggtcgacg    180
aattcaaaaa aa                                                        192

<210> SEQ ID NO 7
<211> LENGTH: 44
<212> TYPE: PRT
<213> ORGANISM: artificial sequence
<220> FEATURE:
<223> OTHER INFORMATION: description of the artificial sequence:
      exendin-4-derivat

<400> SEQUENCE: 7

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 8
<211> LENGTH: 23
<212> TYPE: DNA
<213> ORGANISM: artificial sequence
<220> FEATURE:
<223> OTHER INFORMATION: description of the artificial sequence: primer

<400> SEQUENCE: 8 tttttaagc ttgcacggtg aag                                              23

<210> SEQ ID NO 9
<211> LENGTH: 59
<212> TYPE: DNA
<213> ORGANISM: artificial sequence
<220> FEATURE:
<223> OTHER INFORMATION: description of the artificial sequence: primer

<400> SEQUENCE: 9
cttccatctg tttggacagg tcggaggtga aggtaccttc accgtgcaag cttaaaaaa     59

<210> SEQ ID NO 10
<211> LENGTH: 69
<212> TYPE: DNA
<213> ORGANISM: artificial sequence
<220> FEATURE:
<223> OTHER INFORMATION: description of the artificial sequence: primer

<400> SEQUENCE: 10
ggacggacca ccgttttttca gccattcgat gaacagacga acagcttctt cttccatctg   60
tttggacag                                                             69

<210> SEQ ID NO 11
<211> LENGTH: 69
<212> TYPE: DNA
<213> ORGANISM: artificial sequence
```

```
<220> FEATURE:
<223> OTHER INFORMATION: description of the artificial sequence: primer

<400> SEQUENCE: 11
cgtgcatgct attatcactt tttcttcttt ttcgaaggcg gagcaccgga ggacggacca    60
ccgttttc                                                             69

<210> SEQ ID NO 12
<211> LENGTH: 52
<212> TYPE: DNA
<213> ORGANISM: artificial sequence
<220> FEATURE:
<223> OTHER INFORMATION: description of the artificial sequence: primer

<400> SEQUENCE: 12 tttttgaat tcgtcgacca ggtgcggccg cacgtgcatg ctattatcac tt             52

<210> SEQ ID NO 13
<211> LENGTH: 314
<212> TYPE: DNA
<213> ORGANISM: artificial sequence
<220> FEATURE:
<223> OTHER INFORMATION: description of the artifcial sequence: gene for
      sequence ID N0.14

<400> SEQUENCE: 13
ggaaacagaa ttcatggcgc cgacctcttc ttctaccaaa aagctcaact gcaactggaa    60
cacctgctgc tggacctgca gatgatcctg aacggtatca acaactacaa aaacccgaaa   120
ctgacgcgta tcgacgatga cgataaacac ggtgaaggta ccttcacctc cgacctgtcc   180
aaacagatgg aagaagaagc tgttcgtctg ttcatcgaat ggctgaaaaa cggtggtccg   240
tcctccggtg ctccgccttc gaaaaagaag aaaaagtgat aatagcatgc acgtgcggcc   300
gcaagcttaa aaaa                                                    314

<210> SEQ ID NO 14
<211> LENGTH: 88
<212> TYPE: PRT
<213> ORGANISM: artificial sequence
<220> FEATURE:
<223> OTHER INFORMATION: description of the artificial sequence:
      fusion protein

<400> SEQUENCE: 14

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Ile Asp Asp Asp Lys His Gly Glu
        35                  40                  45

Gly Thr Phe Thr Ser Asp Leu Ser Lys Gln Met Glu Glu Glu Ala Val
    50                  55                  60

Arg Leu Phe Ile Glu Trp Leu Lys Asn Gly Gly Pro Ser Ser Gly Ala
65                  70                  75                  80

Pro Pro Ser Lys Lys Lys Lys Lys
                85

<210> SEQ ID NO 15
<211> LENGTH: 39
<212> TYPE: DNA
<213> ORGANISM: artificial sequence
<220> FEATURE:
```

```
<223> OTHER INFORMATION: description of the artificial sequence: primer

<400> SEQUENCE: 15
cgtatcgacg atgacgataa acacggtgaa ggtaccttc                              39

<210> SEQ ID NO 16
<211> LENGTH: 36
<212> TYPE: DNA
<213> ORGANISM: artificial sequence
<220> FEATURE:
<223> OTHER INFORMATION: description of the artificial sequence: primer

<400> SEQUENCE: 16
gtgtttatcg tcatcgtcga tacgcgtcag tttcgg                                 36

<210> SEQ ID NO 17
<211> LENGTH: 22
<212> TYPE: DNA
<213> ORGANISM: artificial sequence
<220> FEATURE:
<223> OTHER INFORMATION: description of the artificial sequence: primer

<400> SEQUENCE: 17
tgagcggata acaatttcac ac                                                22

<210> SEQ ID NO 18
<211> LENGTH: 41
<212> TYPE: DNA
<213> ORGANISM: artificial sequence
<220> FEATURE:
<223> OTHER INFORMATION: description of the artificial sequence: primer

<400> SEQUENCE: 18 tttttttaagc ttgcggccgc acgtgcatgc tattatcact t                          41

<210> SEQ ID NO 19
<211> LENGTH: 50
<212> TYPE: DNA
<213> ORGANISM: artificial sequence
<220> FEATURE:
<223> OTHER INFORMATION: description of the artificial sequence: primer

<400> SEQUENCE: 19 tttttttgcgg ccgcacgtgc atgctattat catttcgaag gcggagcacc                 50

<210> SEQ ID NO 20
<211> LENGTH: 52
<212> TYPE: DNA
<213> ORGANISM: artificial sequence
<220> FEATURE:
<223> OTHER INFORMATION: description of the artificial sequence: primer

<400> SEQUENCE: 20 tttttttgcgg ccgcacgtgc atgctattat catacgcgaa ggcggagcac cg              52

<210> SEQ ID NO 21
<211> LENGTH: 40
<212> TYPE: DNA
<213> ORGANISM: artificial sequence
<220> FEATURE:
<223> OTHER INFORMATION: description of the artificial sequence: primer

<400> SEQUENCE: 21 tttttttaagc ttctattatt tctgaaggta ttcctcaggg                            40
```

METHOD FOR AMIDATING POLYPEPTIDES WITH BASIC AMINO ACID C-TERMINALS BY MEANS OF SPECIFIC ENDOPROTEASES

CROSS REFERENCE TO RELATED APPLICATION

The present application is 371 of International Application having Serial No. PCT/EP2006/008903, filed on Sep. 13, 2006, which claims priority to German Patent Application No. 10 2005 046 113.1, filed on Sep. 27, 2005, the contents of all which are incorporated herein by reference.

The present invention relates to a process for preparing C-terminally amidated di- or polybasic peptides, in particular those having the biological activity of GLP-1 or analogs or derivatives thereof.

The stability, biomedical availability and duration of action of pharmaceutically relevant peptides and proteins depends to a large extent on the nature of the N- or C-terminal end of the molecule. The half-life of biomolecules is influenced markedly by C-terminal extension with basic amino acids. Particularly good pharmaceutical activities can be achieved if on C-terminal extension with more than one basic amino acid the amino acid at the C-terminal end is an amino amide.

Such peptide-based active substances can be prepared, if the peptides are sufficiently small, directly by a complete chemical synthesis according to a modified Merrifield synthesis protocol. However, limitations emerge when such a peptide is required in large quantities. Thus, the amino acids to be employed in the synthesis must initially be prepared and purified in order subsequently to be suitable after chemical modification as reactants in the peptide synthesis. After removal of the protective groups at the end of the synthesis, the target peptide or product can then be purified and formulated as pharmaceutical. Depending on the composition of the peptide, moreover, neighborhood effects may result during the synthesis in restricted yields, racemization or by-product formation through faulty coupling in individual coupling steps, thus possibly having an adverse effect on the overall yield or the purity of the product. Total synthesis is too complicated for preparing larger quantities of required product. Preparation via alternative, especially biotechnological, processes would therefore be desirable.

Enzymes capable of C-terminal amidation of peptides have been known for a long time. These enzymes are named (Eipper et al. Mol. Endocrinol. 1987 November; 1 (11): 777) as peptidylglycine alpha-amidating enzymes (PAM). The preparation and purification of such PAM enzymes is familiar to the skilled worker and has been described in detail (M. Nogudi et al. Prot. Expr. Purif. 2003, 28: 293). However, the preparation is costly in relation to the preparation of other industrial enzymes such as, for example, trypsin or carboxypeptidase.

An alternative to the "in vitro" amidation by means of PAM emerges when the enzyme is coexpressed in the same host cell with the precursor protein to be amidated. This is achieved by introducing a gene sequence which codes for a PAM activity into the host cell under the control of a host-specific regulatory sequence. This expression sequence can either be incorporated stably into the respective chromosomal DNA sequence, or be present on a second plasmid parallel to the expression plasmid for the target protein, or be integrated as second expression cassette on the same vector, or be cloned in a polycistronic expression approach in phase with the gene sequence which encodes the target protein under the control of the same promoter sequence. However, the described yields are low, so that the preparation of large quantities can be achieved only via corresponding fermentation volumes. This leads to a more costly complexity of purification. In addition, the amidation does not take place quantitatively, so that it is necessary to separate amidated from unamidated required protein. A decision in favor of a secretory preparation process (e.g. Hong et al., Appl Biochem Biotechnol. 2003; 110, p. 113-23) must take account of the fact that proteins with polybasic C terminus are secreted to only a very small extent or not at all.

A further method for amidation is based on the use of protein-specific self-cleavage mechanisms (Cottingham et al. Nature Biotech. Vol. 19, 974-977, 2001). However, it is not easy to control this reaction, and transthioesterification and thus the formation of unwanted products may occur. The relatively large contribution of the fusion protein may have adverse effects on the yield.

The amidation processes described above start from a C terminus of the target peptide which is extended by at least one amino acid glycine or alternatively intein peptide. Peptides with C-terminal lysine can, however, if they comprise no additional lysine or arginine subsequently in the sequence be prepared as a multimeric structure which can subsequently be converted by digestion with trypsin or trypsin-like enzymes into the monomeric unit. High yields can be achieved in this way. This is not possible in the case of the processes described above.

The known biotechnological preparation processes are thus associated with disadvantages, and the object of preparing peptides or proteins which have more than one basic amino acid lysine or arginine at the C terminus and are terminally amidated in large quantities at reasonable cost cannot yet be regarded as satisfactorily solved.

An alternative preparation process would emerge if it were possible to prepare in large quantities a precursor of the target peptide which is truncated by at least one basic amino acid, and subsequently to extend this precursor in an enzyme-catalyzed semisynthesis with lysinamide or argininamide.

Levin et al. (Biochemical Journal 63: 308-16; 1956) describe the effect of trypsin on lysinamide and various polylysinamide peptides. The authors' results show that lysinamide derivatives cannot be converted under the influence of trypsin into high molecular weight lysinamide derivatives because hydrolysis of the intermediately formed amides to the free acid takes place rapidly by comparison with the coupling reaction. It must be concluded therefrom that trypsin-catalyzed semisynthetic processes providing the preparation of peptides with C-linked polylysinamide or poly-argininamide or poly-Lys/Arg mixed sequences are unsuccessful or successful only with low yields.

A peptide chemical process which surprisingly permits trypsin-catalyzed ligation of amidated basic amino acids, analogs or derivatives thereof, to peptides which have a C-terminal basic amino acid with high yields (i.e. >30%) has now been found.

It has additionally been possible to observe for the process of the invention, surprisingly, that introduction of protective groups (cf. Pitraschke et al., Tetrahedron: Asymmetry 9, p 1505-1518, 1998) such as, for example, -Boc (t-butyloxycarbonyl), -Z (benzyloxycarbonyl) or -DDZ (dimethylphenylpropyloxycarbonyl) into the amidated basic amino acids (lysinamide, argininamide) does not lead to an improvement in respect of efficiency and selectivity of the ligation reaction. The process of the invention thus has the advantage that it is possible to dispense with masking with protective groups, thus avoiding losses of yield through removal of the protective group and the disposal of toxic reagents. This results in the process having enormous cost advantages over total chemical synthesis.

One aspect of the invention is thus a process for preparing C-terminally amidated di- or polybasic peptides of the general formula I $$(AA)_n\text{-}X_m\text{—}NH_2 \quad (I),$$

where $(AA)_n$ is a peptide consisting of n amino acids of the same or different type, in which AA is an amino acid or analogs or derivatives thereof;
n is an integer between 3 and 2000; and
X is a basic amino acid or analogs or derivatives thereof;
m is an integer between 2 and 15,
in which
a compound of the general formula II $$(AA)_n\text{-}X_p \quad (II)$$

is reacted with a compound of the general formula III $$(X)_q\text{—}NH_2 \quad (III)$$

in which AA, n and X are as defined above, and
p and q are integers, and $$p+q=m,$$

in the presence of an enzyme having the biological activity of trypsin, and where appropriate the resulting compound of the formula I is subjected to protein chemical purification;
in particular in which m is an integer between 2 and 10, or in which m is an integer between 2 and 6.

A further aspect of the invention is a process described above in which n is an integer between 10 and 1000, or between 15 and 500, or between 20 and 400.

A further aspect of the invention is a process described above in which
a) a fusion peptide which comprises one or more compounds of the formula II as part of the fusion peptide is expressed;
b) the compounds of the formula II are liberated from said fusion peptide by chemical or enzymatic cleavage;
c) the intermediate from step b) is, where appropriate after protein chemical purification, reacted in the presence of an enzyme having the biological activity of trypsin with a compound of the formula III; and
d) where appropriate the resulting compound of the formula I is subjected to protein chemical purification and isolation;

in which in particular the elimination of the compound of the formula II from the fusion protein takes place by means of cyanogen halide, enterokinase, factor Xa, Genenase, thrombin or trypsin; and further preferred the fusion protein is expressed in an expression system selected from the group comprising E. coli, S. carnosus, Salmonella, Bacillus subtilis, Pseudomonas fluorescens, K. lactis, P. pastoris, Schizosaccharomyces pombe and S. cerevisiae.

A further aspect of the invention is a process described above in which said peptides of the general formula I have the biological activity of GLP-1 or derivatives or analogs thereof.

A further aspect of the invention is a process described above in which the compound of the formula I is characterized by the formula IV:

HGEGTFTSDL SKQMEEEAVR LFIEWLKNGG PSSGAPPS(X)$_m$-NH$_2$ (IV);

which in turn can in particular be characterized by the sequences:

(SEQ ID No. 1);
HGEGTFTSDL SKQMEEEAVR LFIEWLKNGG PSSGAPPSKK

KKKK-NH$_2$;

(SEQ ID No. 2);
HGEGTFTSDL SKQMEEEAVR LFIEWLKNGG PSSGAPPSKK-NH$_2$;

(SEQ ID No. 3);
HGEGTFTSDL SKQMEEEAVR LFIEWLKNGG PSSGAPPSKR-NH$_2$;

(SEQ ID No. 4)
HGEGTFTSDL SKQMEEEAVR LFIEWLKNGG PSSGAPPSKK

KKKR-NH$_2$
or (SEQ ID No. 5)
HGEGTFTSDL SKQMEEEAVR LFIEWLKNGG PSSGAPPSRK-NH$_2$.

The invention further relates to compounds of the formula I characterized by the sequences:

(SEQ ID No. 2)
HGEGTFTSDL SKQMEEEAVR LFIEWLKNGG PSSGAPPSKK-NH$_2$;

(SEQ ID No. 3)
HGEGTFTSDL SKQMEEEAVR LFIEWLKNGG PSSGAPPSKR-NH$_2$;

(SEQ ID No. 4)
HGEGTFTSDL SKQMEEEAVR LFIEWLKNGG PSSGAPPSKK

KKKR-NH$_2$
or (SEQ ID No. 5)
HGEGTFTSDL SKQMEEEAVR LFIEWLKNGG PSSGAPPSRK-NH$_2$ their use, especially in depot formulations.

A further aspect of the invention is a medicament comprising one or more of the compounds of the formula I characterized by the sequences:

(SEQ ID No. 2)
HGEGTFTSDL SKQMEEEAVR LFIEWLKNGG PSSGAPPSKK-NH$_2$;

(SEQ ID No. 3)
HGEGTFTSDL SKQMEEEAVR LFIEWLKNGG PSSGAPPSKR-NH$_2$;

(SEQ ID No. 4)
HGEGTFTSDL SKQMEEEAVR LFIEWLKNGG PSSGAPPSKK

KKKR-NH$_2$
or (SEQ ID No. 5)
HGEGTFTSDL SKQMEEEAVR LFIEWLKNGG PSSGAPPSRK-NH$_2$.

The meanings for the purposes of the present invention are:
The term "analog" of an amino acid means a naturally occurring amino acid which is not encoded in the genetic code but is suitable for incorporation into a peptide chain. Examples of analogs of an amino acid are ornithine and citrulline, and also all further non-naturally occurring amino acids which have any basic function in the side chain, such as, for example, 2,4-diaminobutanoic acid; 3-methylornithine; 4-methylornithine, 5-aminoleucine; 4-aminoleucine; 3-aminoleucine; 5-aminonorleucine; 4-amino-norleucine; 3-aminonorleucine; 4-aminonorvaline; 3-aminonorvaline; 6-methyllysine; 5-methyllysine; 4-methyllysine; 3-methyllysine.

The term "derivative" of an amino acid means an amino acid or an analog of an amino acid which is substituted by one or more chemical groups. Examples of such chemical groups are protective groups customary in peptide chemistry, such as -Boc (t-butyloxycarbonyl), -Z (benzyloxycarbonyl), -DDZ (dimethylphenylpropyloxycarbonyl), -Fmoc (N-alpha-(9-fluorenylmethyloxycarbonyl), -2-bromo-Z, -2-chloro-Z, -Tfa (trifluoroacetyl), -nicotinoyl, -4-nitro-Z, -2-picolinoyl, -Tos (4-toluenesulfonyl), -For (formyl), -biotinyl, -dansyl, -Dnp (dinitrophenyl), -Mca (monochloracetyl), -Mtt (N-methyltrityl), -Nde (N-1-(4-nitro-1,3-dioxoindan-2-ylidene)ethyl), -acetimidoyl, -acetyl, -myristoyl, -palmitoyl, N-lithocholyl-γ-glutamyl or -ω-carboxyheptadecanoyl.

Such a group is furthermore a group $C(O)$—$(C_6$-$C_{24})$alkyl, a group $C(O)$—$(C_6$-$C_{24})$alkenyl, a group $C(O)$—$(C_6$-$C_{24})$alkanedienyl, or a group $C(O)$—$(C_6$-$C_{24})$alkanetrienyl, where alkyl, alkenyl, alkanedienyl and alkanedienyl groups where present may be branched or straight-chain. $(C_1$-$C_6)$ Alkyl means a hydrocarbon radical having 1, 2, 3, 4, 5 or 6 C atoms. Examples of $(C_1$-$C_6)$alkyl radicals are methyl, ethyl, n-propyl, isopropyl, (1-methylethyl), n-butyl, isobutyl (2-methylpropyl), sec-butyl (1-methylpropyl), tert-butyl (1,1-dimethylethyl), n-pentyl, isopentyl, tert-pentyl, neopentyl, hexyl. $(C_6$-$C_{24})$Alkyl correspondingly means a hydrocarbon radical having 6 to 24 C atoms. Alkyl radicals may be straight-chain or branched. Preferred $(C_6$-$C_{24})$alkyl radicals are fatty acid residues, for example hexyl, octyl, decanyl, undecanyl, dodecanyl, tridecanyl, tetradecanyl (myristyl), pentadecanyl, hexadecanyl, heptadecanyl, octadecanyl (stearyl), nonadecanyl, eicosanyl, dicosanyl, 9,11-dimethyltridecanyl, 11-methyltridecanyl.

Such a group is furthermore a group $C(O)$-phenyl-$(C_5$-$C_8)$ heteroaryl-phenyl, C(O)-biphenyl or C(O)-terphenyl, where the phenyl, biphenyl, terphenyl or heteroaryl groups are unsubstituted or are substituted by one or two groups selected from the group of $(C_1$-$C_{10})$alkyl or $O(C_1$-$C_{10})$alkyl. In monosubstituted phenyl radicals, the substituent may be present in the 2 position, the 3 position or the 4 position. Disubstituted phenyl may be substituted in the 2,3 position, 2,4 position, 2,5 position, 2,6 position, 3,4 position or 3,5 position. In trisubstituted phenyl radicals, the substituents may be present in the 2,3,4 position, 2,3,5 position, 2,4,5 position, 2,4,6 position, 2,3,6 position or 3,4,5 position. Heteroaryl means for example furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl.

The term "basic amino acid" means lysine, arginine or derivatives or analogs thereof, such as, for example, ornithine or citrulline, preferably lysine or arginine, especially lysine. In this connection, lysine or arginine may, instead of the carboxamide group, be derivatized by one or more of another reactive group, in particular selected from the group of amino ester, peptide ester, anhydride and halide, and be correspondingly employed in the process of the invention.

The term "enzyme having the biological activity of trypsin" means, besides the known and commercially available trypsins from the conventional sources such as rat, cattle, pig, human, dog, mouse, the isoenzymes, derivatives or variants thereof, also enzymes having highly related biochemical properties such as, for example, cathepsin, trypsin from *Fusarium oxysporum* and from *Streptomyces* (*S. griseus, S. exfoliatus, S. erythraeus, S. fradiae* and *S. albidoflavus*), tryptase, mastin, acrosin, kallikrein, hepsin, prostasin I, lysyl endopeptidase (Lys-C) and endoproteinase-Arg-C (clostripain).

It is clear to the skilled person in this connection that this list is not definitive, and further enzymes, isoenzymes, derivatives or variants able specifically to cleave C-terminally to basic amino acids are continually being discovered during biotechnological research. Alternatively, the specificity of enzymes can be altered by peptide chemical modification or mutation at the DNA level (muteins). In addition, the specificity and activity of enzymes can be markedly modified by suitable choice of the reaction conditions.

In the preferred embodiment of the process of the invention, the ability of microorganisms to prepare heterologous peptides is utilized. For this purpose, the desired peptide sequence is translated into the corresponding DNA sequence, which is coupled to a host-specific promoter sequence. It is possible in this case, depending on the expression strategy, to express the target peptide so that it is formed by the cell directly or indirectly as fusion peptide remaining inside the cells.

If a fusion strategy using a suitable fusion peptide is chosen, it is then clear to the skilled worker that the fusion partners must be connected together by a linker, that the specific splitting up of the partners in a way allows so that the desired N terminus of the target peptide is available after processing. For the purposes of the present invention, the target peptide is a compound of the formula II. A large number of possibilities, which are known to the skilled worker and are continually expanded, is available for the design of suitable linkers. If, for example, the amino acid methionine is chosen, a chemical cleavage with cyanogen halide is possible. If, for example, a pentapeptide of the sequence DDDDK is chosen as linker, a cleavage with enterokinase is possible. If, for example, the tetrapeptide sequence IEGR is chosen, the cleavage can take place with factor Xa. With an appropriate design, Genenase® can be used as processing enzyme for peptides whose N terminus start with histidine. If the N terminus is characterized by the dipeptide Gly-Ser, it is possible to choose the tetrapeptide LVPR as linker, so that a recognition and cleavage site for thrombin results. Although an enzyme having the biological activity of trypsin is employed according to the invention for the peptide coupling, the use of such an enzyme is possible in principle even at this point in the process of the invention. Thus, trypsin can initially be used in aqueous medium for eliminating the fusion part of the fusion peptide as long as lysine or arginine is inserted as linker between fusion part and target peptide.

However, it is also possible alternatively for the target peptide, if it is export-compatible, to be secreted into the cell culture medium either in the form of a fusion peptide or in its native form. It is possible to use for this purpose recombinant host cells, especially those of microorganisms, preferably of bacteria or yeasts. If bacterial cells are chosen as expression system, there is the additional option of the target peptide or a corresponding fusion peptide which includes the target peptide, i.e. a compound of the formula II for the purposes of the invention, being directly secreted into the periplasm or into the culture medium. It is clear to the skilled person in this connection that the exportation is frequently restricted if the C-terminal end consists of more than one basic amino acid.

The host organisms and methods available in principle for this purpose are known to the skilled worker (cf., for example, Gellissen, Gerd (ed.) Production of Recombinant Proteins, ISBN 3-527-31036-3). They are also to a large extent commercially available from a large number of suppliers. Representatives which may be mentioned are the companies New England Biolabs, Invitrogen and Roche. The catalog descriptions of such companies include references to literature providing an overview of the technology. It is also clear to the skilled worker in this connection that the range of microorganisms to be used is continually expanding, as is the repertoire of the biotechnological methods. Embodiments which are more specific in this respect are also included in the subject matter of the present invention. Examples of host/vector systems mentioned as representative are the following: bacteria of the type of *E. coli, S. carnosus, Salmonella, Bacillus subtilis* or *Pseudomonas*, especially *Pseudomonas fluorescens*, and yeasts of the type of *K. lactis, P. pastoris, Schizosaccharomyces pombe* and *S. cerevisiae*.

However, the skilled worker is aware that these systems mentioned as examples offer a large number of possible variations which emerge for example from the choice of suitable promoters or other regulatory nucleic acid sequences, the genetic properties of the host cell and of the vectors used (e.g. in relation to the DNA copy number, the choice of the selection means etc.).

The skilled worker is likewise aware that a specific purification process must be adapted for each target peptide, because of its physicochemical properties, when it is intended to be provided in isolated form. This is achieved in principle through suitable combination of known biochemical and biophysical separation methods. It is likewise clear in this connection that new possibilities are continually being opened up for achieving or optimizing the desired successful purification on the basis of novel materials (e.g. for the chromatography).

It may be advantageous for the purposes of the present invention to fuse the precursor peptide with a peptide sequence which, for example, permits purification by affinity chromatography.

For further development of the invention, exendin derivatives as disclosed in US 2004/0106547 have been prepared by way of example. Such peptides derived from exendin may, because of their blood glucose-lowering effect, play an important part in medicament development in the treatment of diabetes or other metabolic disorders which lead for example to obesity. It is therefore worthwhile for pharmaceutical purposes to have such peptides available in appropriate form.

The international patent application WO 02/066628 describes a hirudin derivative which has the amino acids Lys-Arg at the C-terminal end. The antithrombotic effect profile can be modified by amidating the C-terminal arginine. For this purpose, the precursor with C-terminal lysine is prepared and subsequently a coupling reaction with argininamide is carried out according to the invention to result in the amidated hirudin derivative. The precursors can be prepared as described in the application via yeast secretion. For this purpose, for example, the gene sequence for Leu-hirudin described in EP-A 0 324 712 is extended by a codon for lysine, and the procedure described by way of example in the patent is continued to prepare the hirudin extended with lysine. Alternatively, it is also possible to follow the route of secretion of the precursor by bacteria. The technology described in the patent application EP-A 1 216 259 can be used for this purpose, for example.

The following examples serve to illustrate the present invention and are by no means to be interpreted as limiting in relation to the subject matters of the present invention.

EXAMPLE 1

Synthesis of an *E. coli*-specific DNA sequence coding for AVE (1-43)

Firstly the gene sequence SEQ ID No. 6 coding for the peptide AVE (1-43) (SEQ ID No. 7) was prepared:

SEQ ID No. 6:
TTTTTTAAGCTTGCACGGTGAAGGTACCTTCACCTCCGACCTGTCCAAA

CAGATGGAAGAAGAAGCTGTTCGTCTGTTCATCGAATGGCTGAAAAACG

GTGGTCCGTCCTCCGGTGCTCCGCCTTCGAAAAAGAAGAAAAAGTGATA

ATAGCATGCACGTGCGGCCGCACCTGGTCGACGAATTCAAA AAAA

SEQ ID No. 7:
HGEGTFTSDL SKQMEEEAVR LFIEWLKNGG PSSGAPPSKK KKK

The gene sequence was synthesized by means of PCR technology. For this purpose, the following 5 primers were prepared by chemical DNA synthesis. This synthesis took place using the Expedite™ DNA synthesis system (from Applied Biosystems).

a) Primer zp5u has the sequence (SEQ ID No. 8):

5'-TTTTTTAAGCTTGCACGGTGAAG-3'

SEQ ID No. 8 includes the 1-23 region of the sense strand ("sense"). The CAC triplet encodes histidine as first amino acid of the target peptide.

b) Primer zp3a has the sequence (SEQ ID No. 9):

5'-CTTCCATCTGTTTGGACAGGTCGGAGGTGAAGGTACCTTCACCGTG

CAAG CTTAAAAAA-3'

SEQ ID No. 9 includes the 1-59 region of the complementary strain ("antisense").

c) Primer zp3b has the sequence (SEQ ID No. 10):

5'-GGACGGACCACCGTTTTTCAGCCATTCGATGAACAGACGAACAGCT

TCTTCTTCCATCTGTTTGGACAG-3'

SEQ ID No. 10 includes the 40-108 region of the complementary strand ("antisense").

d) Primer zp3c has the sequence (SEQ ID No. 11):

5-CGTGCATGCTATTATCACTTTTTCTTCTTTTTCGAAGGCGGAGCACC

GGAGGACGGACCACCGTTTTTC-3'

SEQ ID No. 11 includes the 91-159 region of the complementary strand ("antisense").

The antisense triplet CTT encodes the last amino acid ($AA_{43}$) of the target peptide.

e) Primer zp3d has the sequence (SEQ ID No. 12):

5'-TTTTTTGAATTCGTCGACCAGGTGCGGCCGCACGTGCATGCTATTA

TCACTT-3'

SEQ ID No. 12 includes the remaining region of the complementary strand ("antisense").

Using the primers, 4 PCR reactions were subsequently carried out under standard conditions at 54° C. In reaction 1, 100 ng of each of the primers zp3c and zp5u were employed. The number of cycles in the PCR was 5. In the second reaction, 1/40 of the reaction was reacted with 100 ng of each of the primers zp5u and zp3b in 10 cycles. In reaction 3, 1/40 of the product of reaction 2 were reacted with 100 ng of each of the primers zp5u and zp3c in a further 10 cycles. Finally, the desired DNA fragment was synthesized in 25 PCR cycles with 1/40 of the yield from reaction 3 and the primers zp5u and zp3d, and its length was checked by gel electrophoresis. The desired DNA fragment was purified and reacted with the restriction enzymes EcoR1 and subsequently with Hind3 in accordance with the manufacturer's (New England Biolabs) information.

In parallel, DNA of the plasmid pUC19 (New England Biolabs) was reacted with the enzymes EcoR1 and Hind3. The fragments of the cleavage mixtures were separated on a 1.2% agarose gel and then the remaining vector fragment from pUC19 and the desired product from reaction 4 were isolated. The purified fragments were ligated together in a T4 ligase reaction at 16° C. overnight. Subsequently, competent E. coli cells (Stratagene, strain E. coli XL10 Gold) were transformed with the ligation mixture and plated out on agar plates comprising 25 mg/l ampicillin. Plasmid DNA was isolated from the individual clones and characterized by DNA sequence analysis.

The plasmid DNA of the desired fragment received the designation pSCHPUCZP1-43 and served as starting material for preparing expression vectors for synthesizing the compounds of the formula I in E. coli K12 cells.

EXAMPLE 2

Construction of an Expression Vector for AVE (1-43)

U.S. Pat. No. 5,496,924, the contents of which are hereby expressly included in the present application by reference, proposes an expression system which in principle permits the preparation of tailored fusion proteins. The advantage of the system is that fusion proteins with a small ballast portion can be prepared. The expression system is used by way of example in the application. Fusion of the sequence segments A-B via the enterokinase recognition sequence DDDDK with AVE (1-43) results in a fusion protein having the following gene sequence and amino acid sequence (SEQ ID No. 13 and No. 14):

```
SEQ ID No. 13:
5'-GGAAACAGAATTCATGGCGCCGACCTCTTCTTCTACCAAAAAGCTC

AACTGCAACTGGAACACCTGCTGCTGGACCTGCAGATGATCCTGAACGG

TATCAACAACTACAAAAACCCGAAACTGACGCGTATCGACGATGACGAT

AAACACGGTGAAGGTACCTTCACCTCCGACCTGTCCAAACAGATGGAAG

AAGAAGCTGTTCGTCTGTTCATCGAATGGCTGAAAAACGGTGGTCCGTC

CTCCGGTGCTCCGCCTTCGAAAAAGAAGAAAAAGTGATAATAGCATGCA

CGTGCGGCCGCAAGCTTAAAAAA-3'
```

The ATG and AAG codons mark the first and last amino acid of the fusion peptide.

```
SEQ ID No. 14:
MAPTSSSTKK TQLQLEHLLL DLQMILNGIN NYKNPKLTRI

DDDDKHGEGT FTSDLSKQME EEAVRLFIEW LKNGGPSSGA

PPSKKKKK
```

The encoded gene sequence was prepared by means of PCR technology. For this purpose, the following primers were synthesized:

1) Primer psw3_zpcolf (SEQ ID No. 15):

```
5'-CGTATCGACGATGACGATAAACACGGTGAAGGTACCTTC-3'
```

The sequence of the primer in this case covers the enterokinase recognition site and the start of the $AVE_{1-43}$-encoding sequence.

2) Primer psw3_zpcolrev (SEQ ID No. 16):

```
5'-GTGTTTATCGTCATCGTCGATACGCGTCAGTTTCGG-3'
```

The sequence in this case corresponds to a synthesic sequence derived from interleukin2 which, as shown in Table I of U.S. Pat. No. 5,496,924, covers amino acids 34-38 and ⅔ of the codon for the amino acid methionine. The remainder of the primer sequence overlaps with primer psw3_zpcolf.

3) pBprimef1 (SEQ ID No. 17):

```
5'-TGAGCGGATAACAATTTCACAC-3'
```

The primer hybridizes upstream with the EcoRI cleavage site which is present in the plasmid pK50 (cf. FIG. 33 in U.S. Pat. No. 5,496,924).

4) psw3_ave__1-43_rev with Hind3 cleavage site (SEQ ID No. 18):

```
5'-TTTTTTAAGCTTGCGGCCGCACGTGCATGCTATTATCACTT
```

Two PCRs were carried out in parallel. One was carried out on DNA of the plasmid pK50 with the primer pair pBprimef1 and psw3_zpcolrev at 50° C. and the other reaction was carried out with the primer pair psw3_zpcolf and psw3_ave__1-43_rev at 54° C. on DNA of the plasmid pSCHPUCZP1-43. The PCR yields were purified after fractionation by gel electrophoresis, and an aliquot of each were mixed in the ratio 1:1 and then reacted in a third PCR with the primer pair pBprimef1 and psw3_ave__1-43_rev. The PCR yield was reacted with the enzymes EcoR1 and Hind3 and employed in a T4 ligase reaction into the plasmid pK50 which was opened in parallel with these enzymes. Competent E. coli BL21 cells are transformed with the ligation mixture and plated out on selective agar comprising 25 mg/l ampicillin. Plasmid DNA was reisolated from some clones and analyzed by PCR and subsequent DNA sequence analysis. Correct plasmids receive the name pBZP43. E. coli BL21:pBZP43 clones are checked for expression of the fusion protein. This takes place in a manner analogous to example 14 of U.S. Pat. No. 5,496,924. The expresssion products were analyzed by mass spectrometry and by SDS-PAGE, and the N terminus was determined by protein sequence analysis. A suitable clone for fermentation of larger quantities of material was selected.

EXAMPLE 3

Construction of an Expression Vector for AVE (1-39)

Plasmid pBZP43 serves as template for the PCR reaction carried out with the primers pBprimef1 (Ex. 2) and psw3_ave__39rev. The PCR product is reacted with restriction enzymes EcoRI and NotI in accordance with the information from the enzyme manufacturer, and inserted in a T4 ligase reaction into the plasmid pBZP43 opened with EcorI/-

NotI. The result is the plasmid pBZP39, with which the procedure described in Example 2 is continued.

psw3_ave_39rev (SEQ ID No. 19):

5'-TTTTTTGCGGCCGCACGTGCATGCTATTATCATTTCGAAGGCGGAGCACC-3'

The TTT triplet encodes lysine in position 39.

EXAMPLE 4

Construction of an Expression Vector for AVE (1-38-Arg)

Plasmid pBZP43 serves as template for the PCR reaction carried out with the primers pBprimef1 (Ex. 2) and psw3_ave38_argrev. The PCR product is reacted with restriction enzymes EcoRI and NotI in accordance with the information from the enzyme manufacturer, and inserted in a T4 ligase reaction into the plasmid pBZP43 opened with EcoRI/NotI. The result is the plasmid pBZP38arg, with which the procedure described in Example 2 is continued.

Primer: psw3_ave38_argrev (SEQ ID No. 20):

5'-TTTTTTGCGGCCGCACGTGCATGCTATTATCATACGCGAAGGCGGAGCACCG-3'

The AGG triplet encodes arginine in position 39.

EXAMPLE 5

Fermentation of the Strains Constructed in Example 2-4

The fermentation took place as described in the German patent application DE 10 2004 058306.4, Ex. 3, with slight differences. *E. coli* BL21 cells transformed with various plasmid vectors coding for target peptide derivatives (fusion protein) were cultivated in mineral salt medium or complex medium (see Example 1) at 30° C. or 37° C. and pH of 7.0 in a fermentor. The pH was adjusted with an $NH_4^+$ solution (26% in water). The aeration of the culture was ensured by a control strategy which kept the dissolved oxygen in the culture broth constant at 30%. For fed batch processes in mineral salt medium, a glucose solution (60% w/v) was fed (8 g/L/h to 26 g/L/h). Protein expression was induced by adding IPTG (1-4 mM final conc. (f.c.)). The duration of induction was 6-8 h. Expression of the target proteins was detected by SDS polyacrylamide gel electrophoresis (SDS-PAGE).

Expression of AVE precursor fusion protein in *E. coli* BL21/pBZP43 was carried out as described below:

100 µL of cell suspension were removed from the continuous culture of *E. coli* BL21 cells stored at −80° C. and incubated in 0.5 L of preculture medium with shaking at 37° C. for 10-16 h. The main culture in the fermentor was inoculated with an appropriate quantity of preculture for an inoculation density of from 0.01 to 0.05 $OD_{600}$.

Preculture medium:
5 g/L Bacto tryptone
10 g/L yeast extract
5 g/L NaCl
Main culture medium:
Defined mineral salt medium (minimal medium) based of glucose as carbon source (Jeffrey H. Miller: Experiments in Molecular Genetics, Cold Spring Harbor Laboratory (1972)).

After the glucose initially present in the main culture medium had been consumed, a glucose solution was fed in. Protein expression was induced by adding IPTG (1 mM f.c.), and the maximum expression of the fusion protein after induction was observed. The SDS-PAGE analytical system from Novex (NuPage® Novex 12% gel system, Invitrogen™) was used for example in accordance with manufacturer's information to analyze in the fermentation in each case 0.02 $OD_{600\ nm}$ of cell suspension removed from the fermentor at various cultivation times.

EXAMPLE 6

Purification of the Fusion Proteins Prepared in Example 5

1000 g of biomass of recombinant *E. coli* strain were resuspended in 1000 ml of Tris buffer (50 mM Tris/HCl, pH 7.4). The cells were disrupted by high-pressure homogenization (Rannie high-pressure homogenizer, 1000 bar) twice. The genomic DNA was digested by adding Benzonase (1000 U/L) and magnesium chloride (10 mM) for 1.5 hours. The fusion protein was purified by expanded bed chromatography. For this purpose, the cell homogenate was diluted to 10 liters with buffer (50 mM Tris/HCl, pH 7.4) and directly loaded onto a chromatography column (Streamline SP XL, GE Healthcare) previously equilibrated with buffer (50 mM Tris/HCl pH 7.4). Sample loading was followed by a washing step with equilibration buffer (6 column volumes), followed by a further washing step with 7% high-salt buffer (50 mM Tris/HCl pH 7.4; 1 M NaCl). Elution took place by washing with 10 column volumes of 20% high-salt buffer. The elution pool was checked by SDS gel electrophoresis (NuPage® Novex 12% gel system, Invitrogen) and HPLC. The fusion protein pool was employed for the protease cleavage reaction after diafiltration into enterokinase buffer (50 mM Tris/HCl pH 7.4; 50 mM NaCl, 2mM $CaCl_2$). The fusion proteins were cleaved by enterokinase (Invitrogen) in enterokinase buffer (20 mM Tris/HCl, 50 mM NaCl, 2 mM $CaCl_2$ pH 7.4) in accordance with the manufacturer's information.

EXAMPLE 7

Separation of the Cleavage Products from the Enterokinase Cleavage Reaction

Separation of the cleavage products takes place in accordance with Example 6 of German patent application DE102004058306.4. Cleavage of the fusion proteins by enterokinase was followed by separation of the cleavage products from one another by ion exchange chromatography (Source 30S, Amersham Biosciences). The ionic strength of the solution was brought to about 7 mS/cm by dilution with $H_2O$. After the protein solution had been loaded onto the previously equilibrated column (20 mM Tris/HCl, pH 7.4; adjusted to a conductivity of about 7 mS/cm with NaCl), unbound material was washed out with 15% buffer B (20 mM Tris/HCl, pH 7.4; 500 mM NaCl). Elution of the AVE peptide precursors took place by applying a gradient over 10 column volumes to 100% buffer B. AVE precursor-containing fractions were identified by SDS gel electrophoresis, HPLC and mass spectrometry. The corresponding fractions were combined, desalted and, after removal of organic solvent, lyophilized.

EXAMPLE 8

Peptide Coupling of AVE (1-39) with H-Lys(Boc)-$NH_2$ 0.2 mg of AVE (1-39) (MW 4218; 0.047 µmol; 1 g/L final concentration) are weighed into a 1.5 mL polypropylene reaction vessel. 11 µL of 0.1 M pyridine-acetate buffer of pH 5.6, 60 µL of a 129 g/L solution of H-Lys(Boc)-NH$_2$.HCl in 0.1 M pyridine-acetate buffer of pH 5.6 (contains 7.75 mg of H-Lys (Boc)-NH$_2$.HCl=27.5 µmol=585 mol of H-Lys(Boc)-NH$_2$.HCl per mole of AVE (1-39)) and 119 µL of DMF are added. The clear solution is equilibrated at 12° C. The reaction is started by adding 10 µL of a 2 g/L trypsin solution in water (contains 0.02 mg of trypsin=0.002 g of trypsin per g of AVE (1-39)). The reaction solution is incubated at 12° C. while shaking at 1000 min$^{-1}$. Samples for process control are taken regularly and stopped by diluting with 9 vol of a solution of 17% water, 17% acetonitrile and 64% trifluoroacetic acid. The progress of the reaction is followed by LC-MS. After the maximum yield is reached, the reaction is acidified to a pH below 2.5 by adding trifluoroacetic acid and is purified by chromatography.

EXAMPLE 9

Peptide Coupling of AVE (1-43) with H-Lys-NH$_2$ 3.85 mg of AVE (1-43) (MW 4731; 0.814 µmol; 20 g/L final concentration) are weighed into a 1.5 ml polypropylene reaction vessel. 41 µL of a 620 g/L solution of H-Lys-NH$_2$.2HCl in 0.1 M sodium acetate buffer of pH 5.8 (contains 25.6 mg of H-Lys-NH$_2$.2HCl=117.5 µmol=144 mol of H-Lys-NH$_2$.2HCl per mole of AVE (1-43)), 116 µL of DMF and 32 µL of 0.1 M sodium acetate buffer of pH 5.8 are added. The clear solution is equilibrated at 12° C. The reaction is started by adding 2.9 µL of a 20 g/L trypsin solution in water (contains 0.06 mg of trypsin=0.015 g of trypsin per g of AVE (1-43)). The reaction solution is incubated at 12° C. while shaking at 900 min$^{-1}$. Samples for process control are taken regularly and stopped by dilution with 9 vol of a solution of 17% water, 17% acetonitrile and 64% trifluoroacetic acid. The progress of the reaction is followed by LC-MS. After the maximum yield is reached, the reaction is acidified to a pH below 2.5 by adding trifluoroacetic acid, and is purified by chromatography.

EXAMPLE 10

Peptide Coupling of AVE (1-39) with H-Lys-NH$_2$ 0.2 mg of AVE (1-39) (MW 4218; 0.047 µmol; 1 g/L final concentration) are weighed into a 1.5 mL polypropylene reaction vessel. 11 µL of 0.1 M pyridine-acetate buffer of pH 5.6, 60 µL of a 100 g/L solution of H-Lys-NH$_2$.2HCl in 0.1 M pyridine-acetate buffer of pH 5.6 (contains 6.0 mg of H-Lys-NH$_2$.2HCl=27.5 µmol=585 mol of H-Lys-NH$_2$.2HCl per mole of AVE (1-39)) and 119 µL of DMF are added. The clear solution is equilibrated at 12° C. The reaction is started by adding 10 µL of a 2 g/L trypsin solution in water (contains 0.02 mg of trypsin=0.002 g of trypsin per g of AVE (1-39)). The reaction solution is incubated at 12° C. while shaking at 1000 min$^{-1}$. Samples for process control are taken regularly and stopped by diluting with 9 vol of a solution of 17% water, 17% acetonitrile and 64% trifluoroacetic acid. The progress of the reaction is followed by LC-MS. After the maximum yield is reached, the reaction is acidified to a pH below 2.5 by adding trifluoroacetic acid and is purified by chromatography.

EXAMPLE 11

Peptide Coupling of AVE (1-39) with H-Arg-NH$_2$ 0.2 mg of AVE (1-39) (MW 4218; 0.047 µmol; 1 g/L final concentration) are weighed into a 1.5 mL polypropylene reaction vessel. 11 µL of 0.1 M pyridine-acetate buffer of pH 5.6, 60 µL of a 113 g/L solution of H-Arg-NH$_2$.2HCl in 0.1 M pyridine-acetate buffer of pH 5.6 (contains 6.77 mg of H-Arg-NH$_2$.2HCl=27.5 µmol=585 mol of H-Arg-NH$_2$.2HCl per mole of AVE (1-39)) and 119 µL of DMF are added. The clear solution is equilibrated at 12° C. The reaction is started by adding 10 µL of a 2 g/L trypsin solution in water (contains 0.02 mg of trypsin=0.002 g of trypsin per g of AVE (1-39)). The reaction solution is incubated at 12° C. while shaking at 1000 min$^{-1}$. Samples for process control are taken regularly and stopped by diluting with 9 vol of a solution of 17% water, 17% acetonitrile and 64% trifluoroacetic acid. The progress of the reaction is followed by LC-MS. After the maximum yield is reached, the reaction is acidified to a pH below 2.5 by adding trifluoroacetic acid and is purified by chromatography.

EXAMPLE 12

Peptide Coupling of AVE (1-43) with H-Arg-NH$_2$ 0.25 mg of AVE (1-43) (MW 4731; 0.047 µmol; 1.1 g/L final concentration) are weighed into a 1.5 mL polypropylene reaction vessel. 11 µL of 0.1 M pyridine-acetate buffer of pH 5.6, 60 µL of a 113 g/L solution of H-Arg-NH$_2$.2HCl in 0.1 M pyridine-acetate buffer of pH 5.6 (contains 6.77 mg of H-Arg-NH$_2$.2HCl=27.5 µmol=585 mol of H-Arg-NH$_2$.2HCl per mole of AVE (1-43)) and 119 µL of DMF are added. The clear solution is equilibrated at 12° C. The reaction is started by adding 10 µL of a 2 g/L trypsin solution in water (contains 0.02 mg of trypsin=0.002 g of trypsin per g of AVE (1-43)). The reaction solution is incubated at 12° C. while shaking at 1000 min$^{-1}$. Samples for process control are taken regularly and stopped by diluting with 9 vol of a solution of 17% water, 17% acetonitrile and 64% trifluoroacetic acid. The progress of the reaction is followed by LC-MS. After the maximum yield is reached, the reaction is acidified to a pH below 2.5 by adding trifluoroacetic acid and is purified by chromatography.

EXAMPLE 13

Peptide Coupling of AVE (1-38)-Arg with H-Lys-NH$_2$ 0.2 mg of AVE (1-38)-Arg (MW 4246; 0.047 µmol; 1 g/L final concentration) are weighed into a 1.5 mL polypropylene reaction vessel. 11 µL of 0.1 M pyridine-acetate buffer of pH 5.6, 60 µL of a 100 g/L solution of H-Lys-NH$_2$.2HCl in 0.1 M pyridine-acetate buffer of pH 5.6 (contains 6.0 mg of H-Lys-NH$_2$.2HCl=27.5 µmol=585 mol of H-Lys-NH$_2$.2HCl per mole of AVE (1-38)-Arg) and 119 µL of DMF are added. The clear solution is equilibrated at 12° C. The reaction is started by adding 10 µL of a 2 g/L trypsin solution in water (contains 0.02 mg of trypsin=0.002 g of trypsin per g of AVE (1-38)-Arg). The reaction solution is incubated at 12° C. while shaking at 1000 min$^{-1}$. Samples for process control are taken regularly and stopped by diluting with 9 vol of a solution of 17% water, 17% acetonitrile and 64% trifluoroacetic acid. The progress of the reaction is followed by LC-MS. After the maximum yield is reached, the reaction is acidified to a pH below 2.5 by adding trifluoroacetic acid and is purified by chromatography.

EXAMPLE 14

Peptide Coupling of AVE (1-43) with H-Lys(Boc)-NH$_2$ 20 mg of AVE (1-43) (MW 4731; 1.058 µmol; 20 g/L final concentration) are weighed into a 2 mL polypropylene reaction vessel. 370 μL of a 482 g/L solution of H-Lys(Boc)-NH$_2$.HCl in 0.1 M sodium citrate buffer of pH 5.5 (contains 155 mg of H-Lys(Boc)-NH$_2$.HCl=550 μmol=130 mol H-Lys (Boc)-NH$_2$.HCl per mole of AVE (1-43)) and 600 μL of DMF are added. The clear solution is equilibrated at 12° C. The reaction is started by adding 30 μL of a 3.3 g/L trypsin solution in water (contains 0.1 mg of trypsin=5 mg of trypsin per g of AVE (1-43)). The reaction solution is incubated at 12° C. while shaking at 1000 min$^{-1}$. Samples for process control are taken regularly and stopped by dilution with 9 vol of a solution of 17% water, 17% acetonitrile and 64% trifluoroacetic acid. The progress of the reaction is followed by LC-MS. After the maximum yield is reached, the reaction is acidified by adding trifluoroacetic acid to a final concentration of 50% (v/v). This stops the reaction and at the same time quantitatively removes the Boc protective group. The reaction product is purified by chromatography.

EXAMPLE 15

Purification of the Amidated AVE Derivatives

The reaction mixture from the coupling reactions is subsequently separated by RP chromatography using Amberchrom CG300 XT 20 as support material, and the amidated target peptide is subsequently isolated from the appropriate eluate fraction by an ion exchange step with Source 30S as support. After desalting on Amberchrom columns, the product is available for formulation as medicament. The identity of the structure of the product was demonstrated by MALDI-MS and NMR analysis.

EXAMPLE 16

Preparation of Leu-hirudin$_{1-65}$ Lys-Arg-NH$_2$

Example 1 of the patent application EP-A 1 216 259 describes the preparation of an expression plasmid which permits the secretion of Leu-hirudin into bacterial supernatants. DNA of the plasmid is employed as template in a standard PCR. The forward primer used in the reaction is the sequence smompaf2 described in the example. The reverse primer used is an oligonucleotide hir_lys66_rev (SEQ ID NO.: 21) which has the following sequence:

```
5'-TTTTTTAAGC TTCTATTATT TCTGAAGGTA TTCCTCAGGG-3'
         Hind3
```

The codon underlined therein codes for lysine. The sequence from position 22 to position 40 (end) is complementary to the sequence segment 178-195 of the sequence depicted in Table 1 of the application EP-A 1 216 259.

As described in the example, the PCR is carried out and the product is digested with the restriction enzymes EcoR1 and Hind3 and inserted into the correspondingly opened vector pJF118. After characterization, DNA is transformed into *E. coli* K12 as in Example 11 of the patent application EP-A 1 216 259, and the intermediate product is expressed and purified. Then, corresponding to Example 13 of the present application, corresponding to the molarities the reaction takes place with argininamide to give Leu-hirudin$_{1-65}$ Lys-Arg-NH$_2$. If the expression is carried out directly in the strain MC1061 used as intermediate host strain, product is found also in the periplasmic space. This makes necessary a cell disruption in accordance with known methods as additional workup step for isolating the intermediate product.

EXAMPLE 17

Analysis of Peptide Coupling Reactions on AVE Derivatives

The coupling reactions according to Examples 8-14 are followed analytically by RP-HPLC on a Symmetry 300 150× 4.6 mm, 5 μm, column from Waters. 0.1% (v/v) formic acid (eluent A) and acetonitrile with 0.1% formic acid (eluent B) serves as eluents. A linear gradient from 20 to 50% B over 15 min at a column temperature of 60° C. and a flow rate of 1 mL/min is used for elution. Detection takes place at 215 nm. Normally 5 μL of a 1:25-diluted reaction sample are injected. The deprotected AVE derivatives are detected at retention times between 7 and 10 min.

The invention claimed is:

1. A process for preparing a C-terminally amidated peptide of the formula (AA)-X—$NH_2$ wherein (AA) is a peptide that comprises an amino acid sequence selected from the group consisting of SEQ ID NO:1 and SEQ ID NO:4 and wherein X is lysine or arginine; the process comprising reacting a peptide having the amino acid sequence of SEQ ID NO:7 with
   (i) H-Arg-$NH_2$ in a 585:1 molar ratio in the presence of an enzyme having the biological activity of trypsin to produce the C-terminally amidated peptide of SEQ ID NO:4, or
   (ii) H-Lys-$NH_2$ in a 144:1 molar ratio in the presence of an enzyme having the biological activity of trypsin to produce the C-terminally amidated peptide of SEQ ID NO:1, and the resulting C-terminally amidated peptide is subjected to protein chemical purification.

2. The process as claimed in claim 1, further comprising
   a) expressing a fusion peptide which comprises a peptide having the sequence SEQ ID NO:7 with a recombinant host cell;
   b) liberating the peptide having the sequence of SEQ ID NO:7 from said fusion peptide by enzymatic cleavage; and
   c) purifying the liberated peptide from step b) and then reacting the purified peptide with H-Arg-$NH_2$ or H-Lys-$NH_2$ in the presence of an enzyme having the biological activity of trypsin; and
   d) subjecting the resulting peptide to protein chemical purification and isolation.

3. The process as claimed in claim 2, in which the liberation from the fusion protein takes place by enzymatic cleavage with enterokinase, factor Xa, Genenase, thrombin or trypsin.

4. The process as claimed in claim 3, in which the fusion protein is expressed in a host/vector expression system selected from the group comprising *E. coil, S. carnosus, Salmonella, Bacillus subtilis, Pseudomonas fluorescens, K. lactis, P. pastoris, Schizosaccharomyces pombe* and *S. cerevisiae*.

5. A medicament comprising the C-terminally amidated peptide of SEQ ID NO:4.

* * * * *